(12) United States Patent
Evans et al.

(10) Patent No.: US 7,048,708 B2
(45) Date of Patent: May 23, 2006

(54) BANDAGE

(75) Inventors: John Christopher Evans, Newhey (GB); Keith Clapham, Nelson (GB)

(73) Assignee: BSN Medical, Inc., Wilmington, DE (US)

( * ) Notice: Subject to any disclaimer, the term of this patent is extended or adjusted under 35 U.S.C. 154(b) by 0 days.

(21) Appl. No.: 10/258,677

(22) PCT Filed: Apr. 24, 2001

(86) PCT No.: PCT/GB01/01825

§ 371 (c)(1),
(2), (4) Date: Nov. 13, 2002

(87) PCT Pub. No.: WO01/80798

PCT Pub. Date: Nov. 1, 2001

(65) Prior Publication Data

US 2003/0120193 A1   Jun. 26, 2003

(30) Foreign Application Priority Data

Apr. 25, 2000   (GB) .................................... 0009805

(51) Int. Cl.
*A61F 13/00*   (2006.01)
(52) U.S. Cl. .......................................... 602/76; 602/75
(58) Field of Classification Search ............ 602/74–79, 602/41, 44, 53, 54; 66/193
See application file for complete search history.

(56) References Cited

U.S. PATENT DOCUMENTS

| 1,257,677 | A |   | 2/1918 | Costello, Jr. |
| 3,523,528 | A |   | 8/1970 | Knohl et al. |
| 3,965,703 | A | * | 6/1976 | Barnhardt ..................... 66/193 |
| 4,207,885 | A | * | 6/1980 | Hampton et al. ............. 602/76 |
| 4,424,808 | A |   | 1/1984 | Schafer et al. |
| 4,734,320 | A |   | 3/1988 | Ohira et al. |
| 5,397,298 | A | * | 3/1995 | Mazza et al. ................. 602/75 |
| 5,540,982 | A |   | 7/1996 | Scholz et al. |
| 5,762,623 | A | * | 6/1998 | Murphy et al. ............... 602/75 |
| 6,156,424 | A | * | 12/2000 | Taylor .................... 428/355 R |
| 2002/0099318 | A1 | * | 7/2002 | Suehr et al. .................. 602/76 |

FOREIGN PATENT DOCUMENTS

| GB | 2 070 656 A |   | 9/1981 |
| GB | 2 178 764 A |   | 2/1987 |
| GB | 2180563 A | * | 4/1987 |

* cited by examiner

*Primary Examiner*—Kim M. Lewis
(74) *Attorney, Agent, or Firm*—Adams Evans P.A.

(57) ABSTRACT

A bandage comprising a weft insertion fabric, in particular a light compression bandage which is a non-laminated and/or single layer bandage comprising a weft insertion fabric or a conformable bandage that essentially consists of a weft insertion fabric, and a method of treating venuous leg, lymphodoema, muscle strain or muscle sprain, which comprises applying such a bandage.

10 Claims, 1 Drawing Sheet

BANDAGE

This application is a national stage application, according to Chapter II of the Patent Cooperation Treaty.

The present invention relates to stretch fabrics and bandages, and in particular to light compression bandages.

Stretch fabrics are often used in the manufacture of bandages to provide bandages with the properties of light support and low compression. Such bandages are often used in the treatment of sprains, strains and venous leg ulcers. The bandages may also be used in sport applications where support is required on a body limb. These bandages should have sufficient elasticity, or stretch, to enable them to conform to the bandaged area and when secured, to allow limited movement and swelling to take place so that the circulation is not adversely affected.

Typical light compression bandages include elastic adhesive bandages (EAB), which traditionally comprise natural yarns, woven to form the fabric. Normally the yarns are woven using a plain weave design. In the manufacturing field of light compression bandages, the simplicity of woven fabrics is preferred over that of knitted fabrics. The woven fabrics of the prior art EABs offer extension in the warp, or length, direction only. Traditionally natural fiber materials were used as these materials were seen as superior to synthetic materials. Although synthetic and/or elastomeric yarns may offer greater initial stretch and superior fatigue resistance than natural yarns, such as cotton, natural yarns have been traditionally preferred for EABs. This is due to the aesthetic appearance of natural yarns and the perceived greater control stretch value, or controlled compression, of natural yarns than synthetic and/or elastomeric yarns.

However, regardless of what types of yarns are used to produce a stretch fabric, the loss of fatigue resistance over time still remains a problem. In particular, the loss of fatigue resistance remains a problem to the previously known light compression bandages, e.g. EABs, which can suffer from loss of fatigue resistance within a few hours of application.

It is an object of the present invention to provide a light compression bandage, which addresses the problems of the prior art light compression bandages.

It is an object of the present invention to provide a light compression bandage, which offers greater conformability than the prior art light compression bandages.

It is a further object of the present invention to provide a light compression bandage, which has greater fatigue resistance than the prior art light compression bandages.

Accordingly, there is provided a bandage comprising a weft insertion fabric.

We also provide a non-laminate and/or single layer bandage comprising a weft insertion fabric.

Further, we provide a conformable bandage that essentially consists of a weft insertion fabric.

We further provide a conformable, non-laminated and/or single layer, bandage comprising a weft insertion fabric.

The term "weft insertion" is known in the art to mean a thread, yarn, filament or the like which is inserted in the weft direction and held in place across the warp direction by pillar threads, yarns, filaments or the like.

We further provide the use of a bandage according to the invention in the treatment or alleviation of venous leg ulcers, lymphodoema, muscle strain or muscle sprain.

In particular we provide a use of a bandage according to the invention for the treatment of venous leg ulcers, lymphodoema, muscle strain or muscle sprain, which comprises applying a bandage according to the invention to an affected site on a patient.

Advantages of the present invention include the improved extension fatigue resistance of the bandage. This enables the bandages to have a longer working life thus saving time and costs as associated with the usage of traditional light compression bandages.

Another advantage of the present invention over the prior art is that the bandages of the present invention have improved conformability. This advantage may be best seen in the weft direction where the improved conformability over the prior art may be the greatest.

Previous light compression bandages, e.g. EABs, have had very little weft extension, if at all. Previously this was not seen as a problem, however surprisingly we have found that the present invention, by having some extension or stretch in the weft direction of the bandage increases conformability of the bandages. If the bandage has too much extension or stretch in the weft direction, as in a full knit fabric or bandage conformability is decreased not increased. Therefore, if a person skilled in the art wanted to increase the stretch of the fabric of the bandage in the weft direction, they would be directed to produce a knit fabric, which may not necessarily increase conformability of the material.

The present invention therefore overcomes this prejudice in the art.

The present invention also makes it feasible to use other yarns besides natural yarns like cotton in the material for the bandage.

Any suitable yarn may be used in the invention although preferably the present invention will comprise a mixture of natural and synthetic yarns.

Typical staple fiber yarns suitable for use in the present invention include cellulosic fiber yarns such as cotton fiber or staple viscose rayon fiber yarns.

Suitable textured filaments for use in composite warp yarns or as textured yarns alone in bandages of the invention include textured filament yarns of synthetic fiber polymers such as polyamide or polyester.

Preferred textured filament yarns for use in the invention are textured filament yarns, e.g. nylon 6,6. Apt yarns of this type are known as 2/78 D Tex nylon.

The composite yarns may comprise a cotton yarn and a textured polyamide yarn; suitably the composite yarn comprises a cotton yarn and a textured yarn twisted together.

Although any suitable yarn may be used, the pillar yarns may comprise synthetic, elastomer and/or natural fibers or filaments, or any combination thereof.

Suitable yarns may include cellulose yarns, e.g. cotton and generic products of cotton, and/or nylon.

Aptly the pillar yarns will contain synthetic and elastomeric fibers or filaments.

Preferably the weft yarns i.e. the weft insertions, will comprise natural yarns, this may include cellulose yarns. Apt yarns for the weft yarns of the present invention may comprise cotton and generic products of cotton.

Other typical yarns suitable as weft yarns of the present invention may comprise rayon or combinations of cotton and rayon.

Bandages according to the invention may comprise one or more inlay yarn for every one composite yarn.

The elastomeric yarn may comprise any natural or synthetic elastomers known per se. Natural elastomers include, for example, natural rubber.

Preferred synthetic elastomers include polyurethane elastomers. Such yarns may comprise 85% polyurethane. Thus, a polyurethane elastomeric yarn need not be 100% polyurethane.

Suitable polyurethane elastomeric yarns include those known as LYCRA (Trade Mark).

Other favored polyurethane elastomeric yarns are ones, which have restricted stretching properties.

For example, preferred polyurethane elastomeric yarns are those, which are wrapped with a less elastic filament, i.e. a cotton or a synthetic wrapping.

The yarns used in the present invention, both for the pillar yarns and the weft insertion may be twisted to give further elastic properties to the yarn or to simply combine more than one yarn to form the composite yarn.

The twist level for the composite yarn can suitably be from 60 to 800 turns/meter, preferably less than 600 turns/meter and preferably more than 200 turns/meter.

Preferably, the bandages of the present invention will have an adhesive to aid holding of the bandage to the user. Clearly any adhesive used should be capable of adhering to that part of the body to which it is to be attached and to adjacent overlapping turns of the bandage.

Preferably the adhesive will be a pressure sensitive adhesive. By the term "pressure sensitive adhesive", it is intended to mean an adhesive, which is inherently tacky, visco-elastic and cohesive in its normal dry state.

The adhesive may be applied wholly or partly to one face of the bandage. However, preferably the adhesive layer should cover most of the area of one face of the bandage.

The adhesive, if used, may be a water permeable or water impermeable adhesive. Preferred water impermeable adhesives include natural rubber latex based adhesives, synthetic rubber based adhesives and hot-melt adhesives. Less preferred water impermeable adhesives include polyvinyl ethers and certain acrylate ester copolymers containing hydrophilic groups.

The light compression bandages of the present invention will now be illustrated, but by no way limited, by reference to the following drawings.

Figure 1:
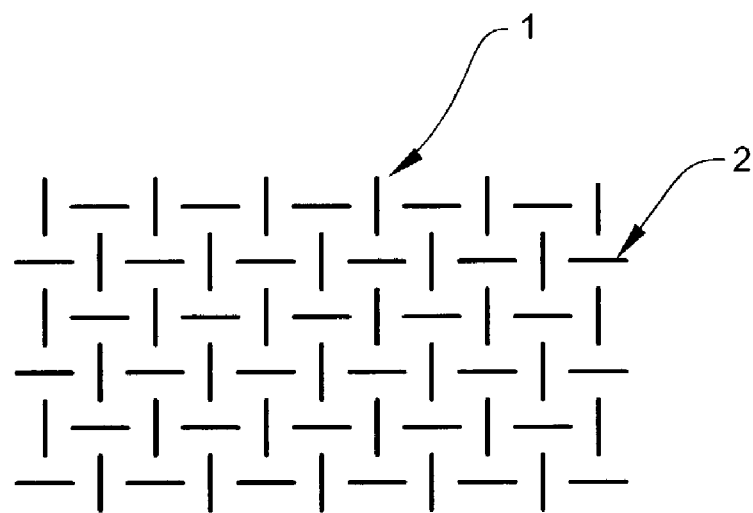
FIG. 1 is a schematic view of the basic structure of a typical traditional woven bandage of the prior art.

In FIG. 1 the basic structure of a typical woven fabric bandage is shown, with warp yarns (1) and a weft yarns (2) that cross back and forth across the warp direction of the bandage, and down the warp direction of the bandage at each pick.

Figure 2:
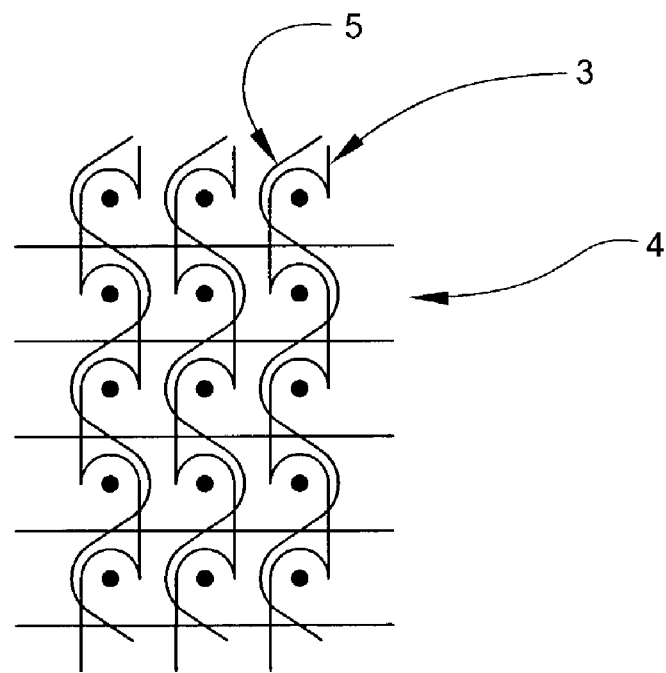
FIG. 2 is a schematic view of the basic structure of a light compression bandage of the present invention.

FIG. 2 shows the basic structure of the bandage of the present invention with weft inserts (4) and pillar yarns comprising a first yarn (3) and a second yarn (5).

This embodiment of the present invention therefore shows loops in the warp direction but has a straight yarn in the weft direction. The weft ends do not loop but are free, like the cut ends of woven products. Fabric or bandages of this embodiment of the present invention may therefore resemble woven products in appearance.

The present invention will now be illustrated by the following examples.

EXAMPLE 1

A light support compression bandage of the invention was formed from a fabric produced on a Paschel/Tricot high-performance warp-knitting machine suitable for weft insertion using a cotton/elastomeric composite yarn for the pillar yarns and a cotton/rayon yarn for the weft insertions.

The composite yarns used in this example for the pillar yarns were 19.68 Tex staple fiber cotton yarn and 1/78 D Tex elastomeric yarn respectively. The composite warp yarns contain the cotton and elastomeric yarns twisted together. The yarns used for the weft insertions were 19.68 Tex fiber cotton yarn and 29.8 Tex rayon yarn.

The bandage was 10 cm wide and comprised 71 ends/10 cm for the pillar yarns. This bandage when applied to a limb at approximately 30% extension caused a compressive force on the limb of 30 mmHg.

The invention claimed is:

1. A compression bandage for being wound about and conforming to a patient's appendage, and comprising a single layer, weft-insertion fabric which consists essentially of relatively elastic warp yarns and relatively inelastic weft insertion yarns, wherein said weft insertion yarns exhibit stretch in a weft direction, and wherein the fabric shows loops in the warp direction but has straight yarns in the weft direction and wherein the weft insertion yarn ends do not loop but are free.

2. The compression bandage of claim 1 further including an adhesive disposed on at least one surface thereof.

3. The compression bandage of claim 1 wherein said warp yarns are composite yarns including cotton fibers and synthetic elastomeric fibers.

4. The compression bandage of claim 3 wherein said weft insertion yarns are twisted cotton fibers.

5. A compression bandage having first and second opposed faces, said bandage comprising:
   a base which consists essentially of a single layer of woven, weft-insertion fabric having pillar yarns and weft yarns, wherein said pillar yarns comprise a combination of cotton fibers and synthetic elastic fibers, and said weft yarns comprise fibers having a stretch, such that said fabric exhibits some stretch in the weft direction; and wherein the fabric shows loops in the warp direction but has straight yarns in the weft direction and wherein the weft insertion yarn ends do not loop but are free end; and
   a layer of adhesive applied to one of said first and second faces.

6. The compression bandage of claim 5 wherein said pillar yarns are composite yarns of natural fibers and synthetic elastomeric fibers.

7. The compression bandage of claim 6 wherein said weft insertion yarns and twisted cotton fibers.

8. A compression bandage having first and second opposed faces, said bandage consisting essentially of:
   a single layer of woven, weft-insertion fabric having pillar yarns and weft yarns, wherein said pillar yarns comprise a combination of inelastic and elastic fibers, and said weft yarns comprise natural fibers;
   said fabric having stretch in a weft direction, wherein the fabric shows loops in the warp direction but has straight yarns in the weft direction and wherein the weft insertion yarn ends do not loop but are free; and
   an adhesive carried by one of said first and second faces.

9. The compression bandage of claim 8 wherein said warp yarns are composite yarns including natural fibers and synthetic elastomeric fibers.

10. The compression bandage of claim 8 wherein said adhesive is a pressure-sensitive adhesive.

* * * * *

UNITED STATES PATENT AND TRADEMARK OFFICE
CERTIFICATE OF CORRECTION

| | | |
|---|---|---|
| PATENT NO. | : 7,048,708 B2 | Page 1 of 1 |
| APPLICATION NO. | : 10/258677 | |
| DATED | : May 23, 2006 | |
| INVENTOR(S) | : John Christopher Evans and Keith Clapman | |

It is certified that error appears in the above-identified patent and that said Letters Patent is hereby corrected as shown below:

Column 4, line 34, delete the word "a" after the word "having".

Column 4, line 39, delete "end".

Signed and Sealed this

Twenty-first Day of November, 2006

JON W. DUDAS
*Director of the United States Patent and Trademark Office*